(12) United States Patent
Tokita et al.

(10) Patent No.: US 9,131,903 B2
(45) Date of Patent: Sep. 15, 2015

(54) DIABETES TREATMENT SUPPORT APPARATUS, DIABETES TREATMENT SUPPORT METHOD, DIABETES TREATMENT SUPPORT PROGRAM

(71) Applicant: OMRON HEALTHCARE CO., LTD., Muko-shi, Kyoto (JP)

(72) Inventors: Muneo Tokita, Kyoto (JP); Satoshi Nakajima, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 0 days.

(21) Appl. No.: 14/377,737

(22) PCT Filed: Nov. 12, 2012

(86) PCT No.: PCT/JP2012/079284
§ 371 (c)(1),
(2) Date: Aug. 8, 2014

(87) PCT Pub. No.: WO2013/136585
PCT Pub. Date: Sep. 19, 2013

(65) Prior Publication Data
US 2015/0038816 A1 Feb. 5, 2015

(30) Foreign Application Priority Data

Mar. 12, 2012 (JP) ................. 2012-054382

(51) Int. Cl.
*A61B 5/00* (2006.01)
*A61B 5/145* (2006.01)
(Continued)

(52) U.S. Cl.
CPC ............ *A61B 5/7278* (2013.01); *A61B 5/1473* (2013.01); *A61B 5/14532* (2013.01);
(Continued)

(58) Field of Classification Search
CPC ... C12Q 1/00–1/006; C12Q 1/26; C12Q 1/32; C12Q 1/54; A61B 5/1427; A61B 5/14532; A61B 5/1468–5/1477; A61B 5/1486–5/14865; A61B 5/4833; A61B 5/7278–5/7282; A61B 5/74–5/7495; G01N 27/327–27/3278; G01N 33/327–33/3278; G01N 2800/042; G01F 15/0275; G01F 15/0283; G06F 9/06–9/548; G06F 19/30; G06F 7/38; G06F 7/388; G06F 7/491–7/4917
See application file for complete search history.

(56) References Cited

U.S. PATENT DOCUMENTS

2010/0330598 A1* 12/2010 Thukral et al. .................. 435/14
2012/0059673 A1    3/2012 Cohen et al.

FOREIGN PATENT DOCUMENTS

JP    A-2001-245900    9/2001
JP    A-2005-326943    11/2005
(Continued)

OTHER PUBLICATIONS

International Search Report issued in International Application No. PCT/JP2012/079284 dated Dec. 11, 2012 (with translation).

*Primary Examiner* — J. Christopher Ball
(74) *Attorney, Agent, or Firm* — Oliff PLC

(57) ABSTRACT

A control unit obtains, from a memory unit, data of a plurality of pre-meal blood sugar levels that are blood sugar levels measured before meals and data of a plurality of post-meal blood sugar levels that are blood sugar levels measured after meals, calculates a pre-meal average value that is an average value of the plurality of pre-meal blood sugar levels, calculates a post-meal average value that is an average value of the plurality of post-meal blood sugar levels, calculates an average blood sugar level that is an average of the pre-meal average value and the post-meal average value, calculates an estimated HbA1c value using the average blood sugar level, and displays the calculated estimated HbA1c value in a display unit.

8 Claims, 6 Drawing Sheets

(51) Int. Cl.
  *A61B 5/1473* (2006.01)
  *G01N 27/416* (2006.01)
  *G01N 33/66* (2006.01)
  *G01N 33/72* (2006.01)
  *G06F 19/00* (2011.01)

(52) U.S. Cl.
  CPC ............. *A61B5/14546* (2013.01); *A61B 5/486* (2013.01); *A61B 5/4866* (2013.01); *A61B 5/7282* (2013.01); *A61B 5/742* (2013.01); *G01N 27/416* (2013.01); *G01N 33/66* (2013.01); *G01N 33/72* (2013.01); *G06F 19/3406* (2013.01); *G01N 2800/042* (2013.01)

(56) References Cited

FOREIGN PATENT DOCUMENTS

| | | |
|---|---|---|
| JP | A-2007-304088 | 11/2007 |
| JP | A-2008-229331 | 10/2008 |
| JP | A-2008-232775 | 10/2008 |
| JP | A-2010-042261 | 2/2010 |
| JP | A-2012-024439 | 2/2012 |
| WO | WO 2006/009199 A1 | 1/2006 |

* cited by examiner

DIABETES TREATMENT SUPPORT APPARATUS, DIABETES TREATMENT SUPPORT METHOD, DIABETES TREATMENT SUPPORT PROGRAM

TECHNICAL FIELD

The present invention relates to diabetes treatment support apparatuses, diabetes treatment support methods, and diabetes treatment support programs.

BACKGROUND ART

Controlling one's blood sugar is the most important aspect in the treatment of diabetes. HbA1c (glycohemoglobin (glycated hemoglobin) A1c) is one example of a blood sugar level indicator. HbA1c is hemoglobin to which the sugar bonds non-enzymatically, and while HbA1c is not affected by short-term changes in blood sugar after meals and the like, the percentage of bonds increases when a high-blood sugar state continues for a long period of time, which causes HbA1c to increase. Hemoglobin has a lifespan of approximately 120 days, and as such, HbA1c is used as an indicator of the blood sugar state one to two months prior to measurement.

Normally, a diabetes outpatient has his/her HbA1c measured once a month when visiting a clinic or the like, and his/her blood sugar state is evaluated by comparing the currently-measured HbA1c with the previous month's measurement value. A course of medication-based treatments is set and dietary/exercise regimens are provided based on the evaluation, and the diabetes patient works to bring his/her HbA1c to a normal value. As such, diabetes patients themselves take considerable interest in changes in their HbA1c.

Thus HbA1c is an extremely important item among indicators of blood sugar states, and is a value of considerable interest to both medical workers and patients alike. However, HbA1c is normally measured at a hospital, using a large measurement device, by collecting the patient's blood. Small-sized devices that measure HbA1c are not widespread, and thus patients cannot know their HbA1c values until they undergo an examination at a hospital.

Furthermore, dedicated small-sized devices for measuring HbA1c are expensive, and require several ul of blood for measurement, which is much higher than the amount required by a blood sugar monitor (1 ul or less). Furthermore, HbA1c by nature changes little from day to day, and thus such a dedicated small-sized device will likely be used comparatively infrequently.

However, even if the device is used infrequently, HbA1c is useful in the self-management of diabetes if it can be measured or checked by the patient him/herself in the same manner as his/her blood sugar level.

In addition to direct measurement using a dedicated measurement device, an estimated value for HbA1c can also be calculated using a plurality of instances of blood sugar level data, as indicated in Patent Literature 1 and 2.

Patent Literature 1 discloses a method in which an average blood sugar level for a given day is calculated from blood sugar level data measured seven times a day, namely before and after breakfast, lunch, and dinner and before going to bed, and an estimated HbA1c value is then calculated based on the average blood sugar level.

Patent Literature 2 discloses a blood sugar monitor having a function for calculating an estimated HbA1c from a plurality of instances of blood sugar level data.

Meanwhile, a blood sugar monitor that outputs an average value of a blood sugar level is known. Patent Literature 3 discloses a blood sugar monitor that divides blood sugar level data found in time series and stored into pre- and post-mealtime groups and outputs an average blood sugar level for each group.

Furthermore, a blood sugar level measurement system that makes it possible to manage the timing of blood sugar level measurements, manage shifts in blood sugar level, and accurately and easily predict future blood sugar levels has been proposed (see Patent Literature 4).

Patent Literature 4 proposes finding individual average values of blood sugar levels at each of seven measurement points, namely before and after breakfast, lunch, and dinner and before going to bed, and furthermore finding a seven-point average value that is the average value of the seven individual average values; the number of times the blood sugar is measured is then reduced based on a correlation coefficient indicating a correlation between the seven-point average value and the respective individual average values.

CITATION LIST

Patent Literature

Patent Literature 1: JP 2008-232775A
Patent Literature 2: JP 2007-304088A
Patent Literature 3: JP 2001-245900A
Patent Literature 4: International Publication WO 06/9199

SUMMARY OF INVENTION

Technical Problem

As described in Patent Literature 2, a blood sugar monitor capable of calculating an estimated HbA1c value from measured blood sugar level data and notifying a user of that estimated value has already been proposed.

However, patients measure their blood sugar levels at different frequencies and at different times, and thus it is difficult to improve the reliability of the estimated HbA1c value when simply calculating the estimated HbA1c value through a conventionally-known computation method.

For example, it is conceivable that the number of instances of blood sugar level data measured after meals will differ greatly from the number of instances of blood sugar level data measured before meals. In such a case, simply finding an average of the blood sugar levels results in the blood sugar level data from the measurements with the greater amount of data taking precedence, and that average will differ greatly from the actual average blood sugar level.

Accordingly, the methods for calculating the estimated HbA1c value disclosed in Patent Literature 1 and 2 cannot bring the estimated HbA1c value closer to an accurate value.

Meanwhile, although Patent Literature 3 and 4 disclose methods for averaging the blood sugar level, the documents do not disclose methods for calculating an estimated HbA1c value from a plurality of instances of blood sugar level data.

Having been achieved in light of such a situation, it is an object of the present invention to provide a diabetes treatment support apparatus, a diabetes treatment support method, and a diabetes treatment support program capable of calculating a highly-reliable estimated HbA1c value from a plurality of instances of blood sugar level data.

Solution to Problem

A diabetes treatment support apparatus according to the present invention is a diabetes treatment support apparatus that calculates an estimated HbA1c value using a plurality of instances of blood sugar level data accumulated in a storage unit, and includes: a data obtainment unit that obtains, from the storage unit, data of a plurality of pre-meal blood sugar levels that are blood sugar levels measured before meals and data of a plurality of post-meal blood sugar levels that are blood sugar levels measured after meals; a pre-meal average calculation unit that calculates a pre-meal average value that is an average value of the plurality of pre-meal blood sugar levels obtained by the data obtainment unit; a computation unit that finds a post-meal average value that is an average value of the plurality of post-meal blood sugar levels obtained by the data obtainment unit or finds a maximum post-meal blood sugar level that is a maximum value in the plurality of post-meal blood sugar levels; an average blood sugar level calculation unit that calculates an average blood sugar level using the pre-meal average value and using the post-meal average value or the maximum post-meal blood sugar level; an estimated HbA1c value calculation unit that calculates the estimated HbA1c value using the average blood sugar level; and an output unit that outputs the calculated estimated HbA1c value.

A diabetes treatment support method according to the present invention is a diabetes treatment support method that calculates an estimated HbA1c value using a plurality of instances of blood sugar level data accumulated in a storage unit, the method including: a data obtainment step of obtaining, from the storage unit, data of a plurality of pre-meal blood sugar levels that are blood sugar levels measured before meals and data of a plurality of post-meal blood sugar levels that are blood sugar levels measured after meals; a pre-meal average calculation step of calculating a pre-meal average value that is an average value of the plurality of pre-meal blood sugar levels that have been obtained; a computation step of finding a post-meal average value that is an average value of the plurality of post-meal blood sugar levels that have been obtained or finding a maximum post-meal blood sugar level that is a maximum value in the plurality of post-meal blood sugar levels; an average blood sugar level calculation step of calculating an average blood sugar level using the pre-meal average value and using the post-meal average value or the maximum post-meal blood sugar level; an estimated HbA1c value calculation step of calculating the estimated HbA1c value using the average blood sugar level; and an output step of outputting the calculated estimated HbA1c value.

A diabetes treatment support program according to the present invention is a program for causing a computer to execute the steps of the aforementioned diabetes treatment support method.

Advantageous Effects of Invention

According to the present invention, a diabetes treatment support apparatus, a diabetes treatment support method, and a diabetes treatment support program capable of calculating a highly-reliable estimated HbA1c value from a plurality of instances of blood sugar level data can be provided.

DESCRIPTION OF EMBODIMENTS

Hereinafter, an embodiment of the present invention will be described with reference to the drawings.

Figure 1:
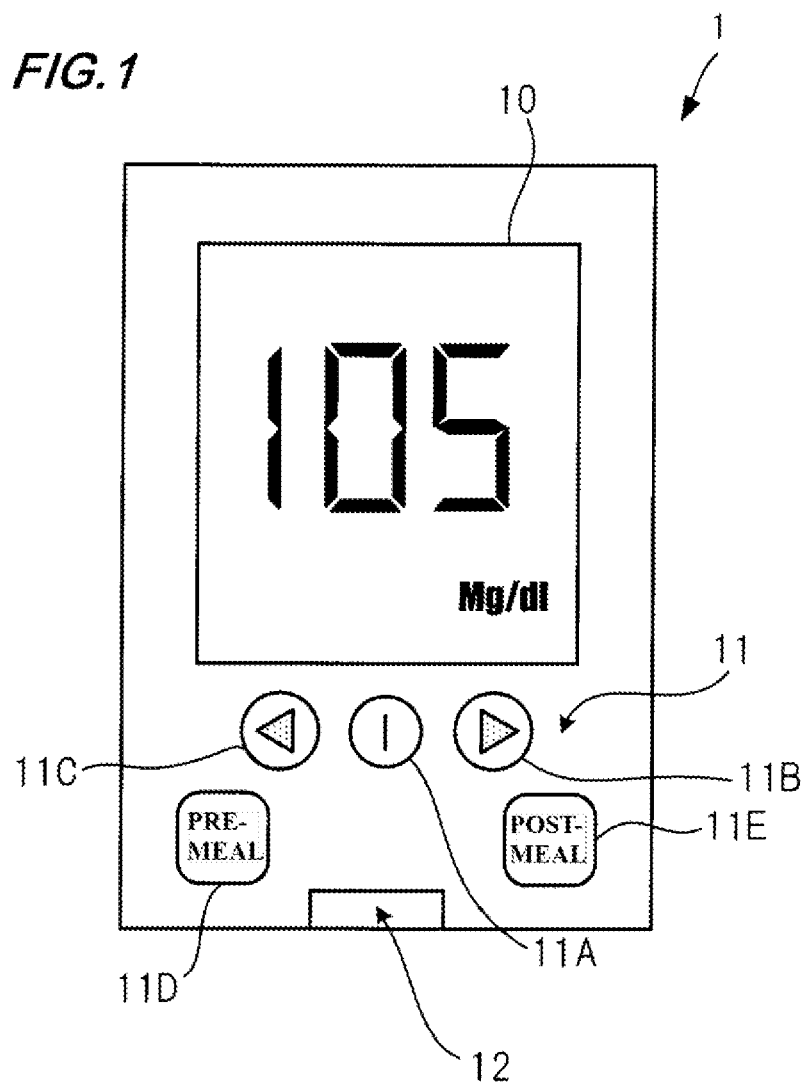
FIG. 1 is an external view illustrating the configuration of a blood sugar monitor 1 serving as an example of a diabetes treatment support apparatus embodying the present invention.

FIG. 1 is an external view illustrating the configuration of a blood sugar monitor 1 serving as an example of a diabetes treatment support apparatus embodying the present invention.

The blood sugar monitor 1 has a configuration in which a display unit 10, an operating section 11, and an electrode insertion section 12 are provided in a housing. The housing is approximately the size of the palm of a hand, and thus the blood sugar monitor 1 can be transported with ease.

The electrode insertion section 12 is an opening into which an electrode for measuring a blood sugar level is inserted. The blood sugar level can be measured via this electrode by bringing one end of the electrode into contact with a measurement subject's blood while the other end of the electrode is inserted into the electrode insertion section 12.

The display unit 10 displays various types of information, including measured blood sugar level data, an operating menu, and so on, and is configured of a liquid crystal display or the like.

The operating section 11 includes a main operating button 11A, toggle buttons 11B and 11C, a pre-meal button 11D, and a post-meal button 11E.

The main operating button 11A is a button for powering on the blood sugar monitor 1, executing instructions through various types of menus, and so on.

The toggle buttons 11B and 11C are buttons for toggling the information displayed in the display unit 10, selecting various types of menus, and so on.

The pre-meal button 11D is a button for inputting pre-meal information, indicating that the timing of a blood sugar level measurement is before a meal, into the blood sugar monitor 1.

The post-meal button 11E is a button for inputting post-meal information, indicating that the timing of a blood sugar level measurement is after a meal, into the blood sugar monitor 1.

Figure 2:
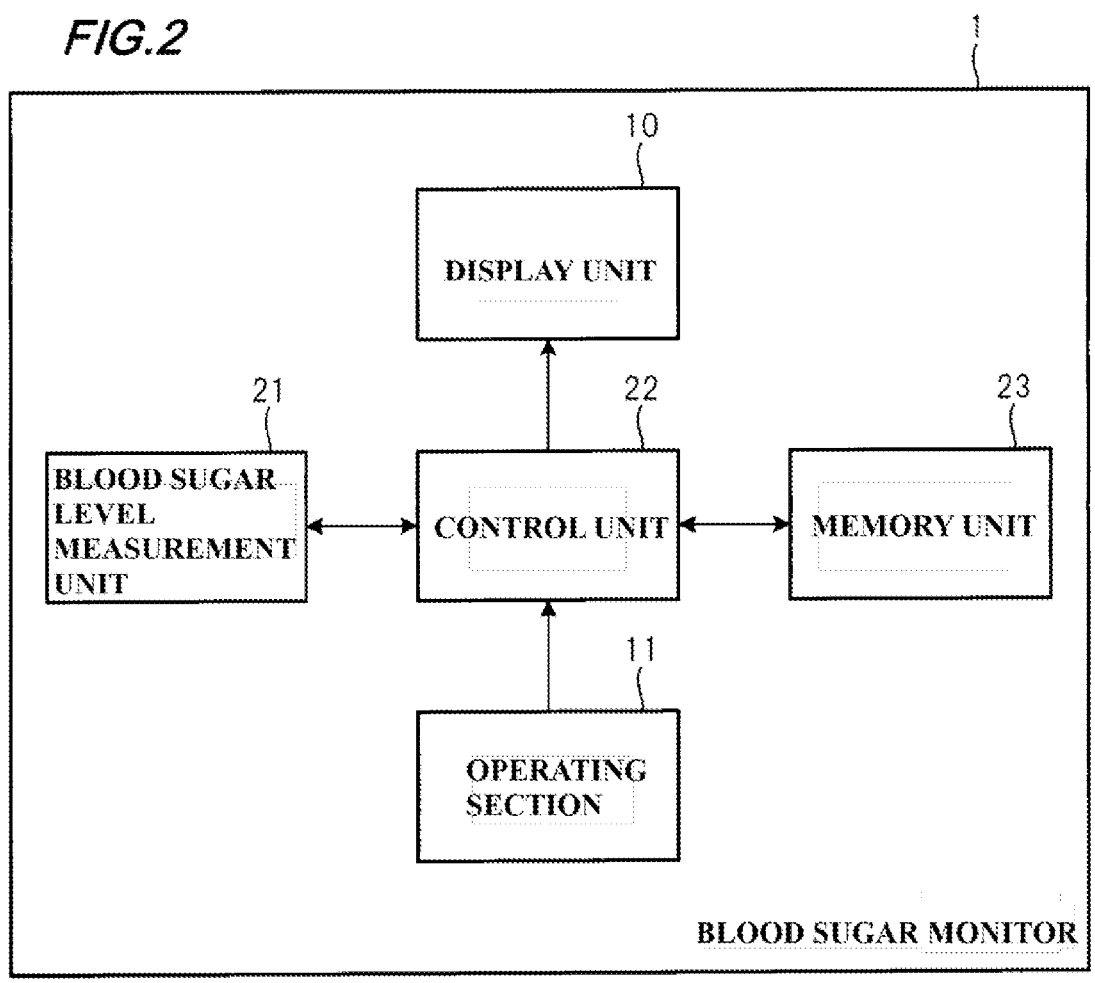
FIG. 2 is a block diagram illustrating the internal configuration of the blood sugar monitor 1 shown in FIG. 1.

FIG. 2 is a block diagram illustrating the internal configuration of the blood sugar monitor 1 shown in FIG. 1.

In addition to the operating section 11 and the display unit 10 shown in FIG. 1, the blood sugar monitor 1 includes a blood sugar level measurement unit 21, a control unit 22, and a memory unit 23.

The blood sugar level measurement unit 21 measures the blood sugar level using the electrode inserted into the electrode insertion section 12 and sends data of the measured blood sugar level to the control unit 22.

The control unit 22 controls the blood sugar monitor 1 as a whole and executes various types of computations, and is configured of a central processing unit (CPU) and a read-only memory (ROM) and random access memory (RAM) connected to the CPU.

The operating section 11 is connected to the control unit 22, and when the operating section 11 is operated, an instruction signal resulting from the operation is inputted to the control unit 22.

The memory unit 23 is a flash memory or the like, for example, in which the blood sugar level data measured by the blood sugar level measurement unit 21 is stored under the control of the control unit 22.

In the blood sugar monitor 1, the control unit 22 has a function for estimating the HbA1c using the plurality of instances of blood sugar level data measured by the blood sugar level measurement unit 21 and stored in the memory unit 23, and outputting the estimated HbA1c (an HbA1c display mode). This function makes it possible to effectively support diabetes treatment. Operations of the blood sugar monitor 1 will be described hereinafter.

Figure 3:
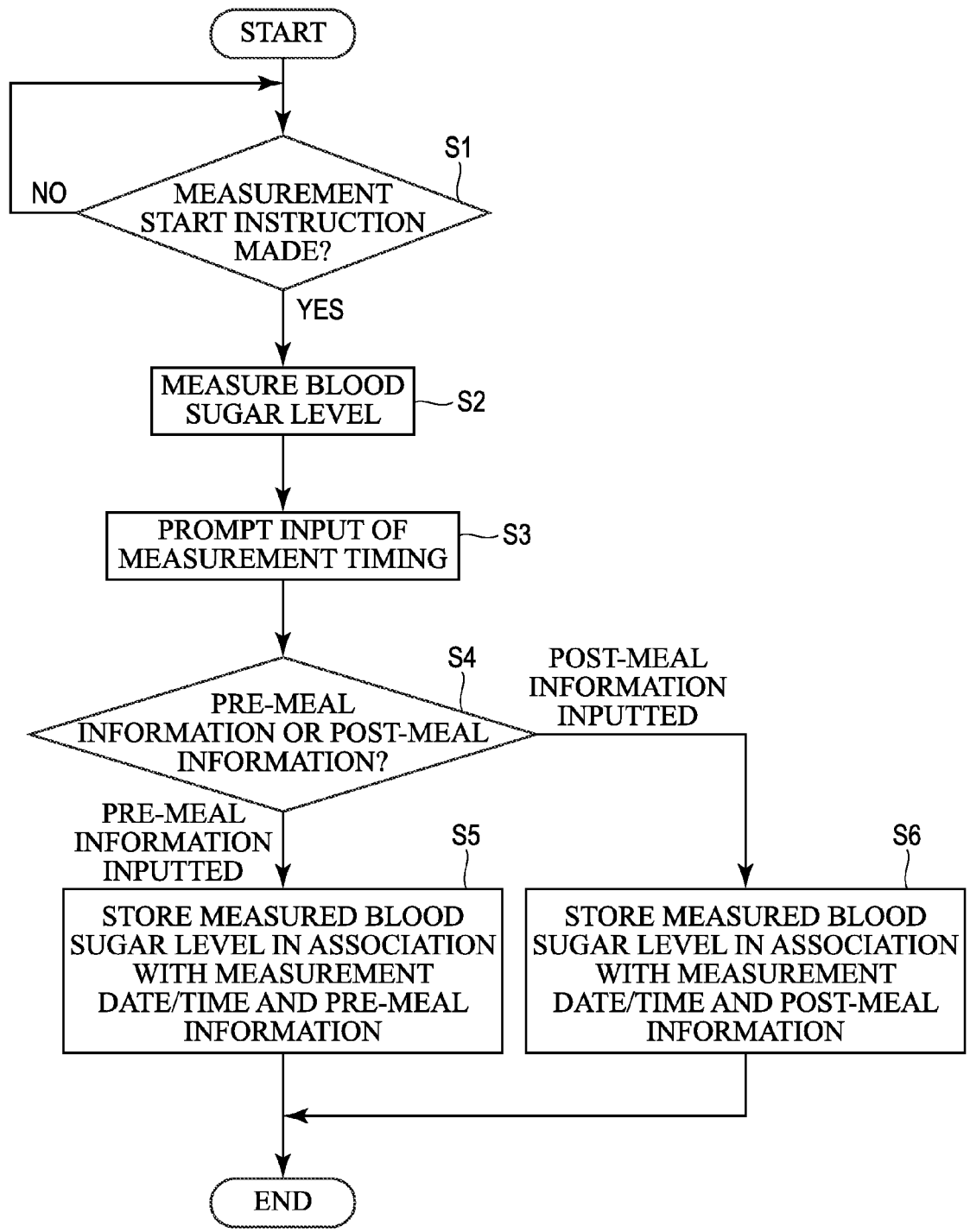
FIG. 3 is a flowchart illustrating operations performed when the blood sugar monitor 1 shown in FIG. 1 measures a blood sugar level.

FIG. 3 is a flowchart illustrating operations performed when the blood sugar monitor 1 shown in FIG. 1 measures a blood sugar level. The steps shown in FIG. 3 are realized by the CPU of the control unit 22 executing a program stored in the ROM.

When the main operating button 11A is pressed and held down, for example, a power on instruction is inputted to the control unit 22, and the blood sugar monitor 1 is turned on as a result.

When the power is turned on, the control unit 22 waits for an instruction to start measuring the blood sugar level. Then, when the main operating button 11A, for example, is pressed and the instruction to start measuring the blood sugar level is inputted to the control unit 22 (step S1: YES), the control unit 22 starts measuring the blood sugar level using the blood sugar level measurement unit 21 in response to the instruction to start the measurement (step S2).

When the blood sugar level measurement ends, the control unit 22 causes a message reading, for example, "please use the pre-meal button or post-meal button to indicate the time of measurement" to be displayed in the display unit 10, thus prompting the measurement subject to input the measurement timing (step S3).

After step S3, in the case where the measurement subject has pressed the pre-meal button 11D, the pre-meal information is inputted to the control unit 22. When the pre-meal information is inputted, the control unit 22 associates the blood sugar level data measured and obtained in step S2 with the pre-meal information and information indicating the measurement date and time of the blood sugar level measured in step S2, and stores the associated data and information in the memory unit 23 (step S5).

After step S3, in the case where the measurement subject has pressed the post-meal button 11E, the post-meal information is inputted to the control unit 22. When the post-meal information is inputted, the control unit 22 associates the blood sugar level data measured and obtained in step S2 with the post-meal information and information indicating the measurement date and time of the blood sugar level measured in step S2, and stores the associated data and information in the memory unit 23 (step S6).

Note that in the case where neither the pre-meal information nor the post-meal information has been inputted within a set amount of time after the blood sugar level measurement has ended, the control unit 22 associates the blood sugar level data obtained through the measurement performed in step S2 with information indicating the measurement date/time and stores the associated data and information in the memory unit 23.

By repeating such operations, the blood sugar level data is accumulated in the memory unit 23.

Figure 4:
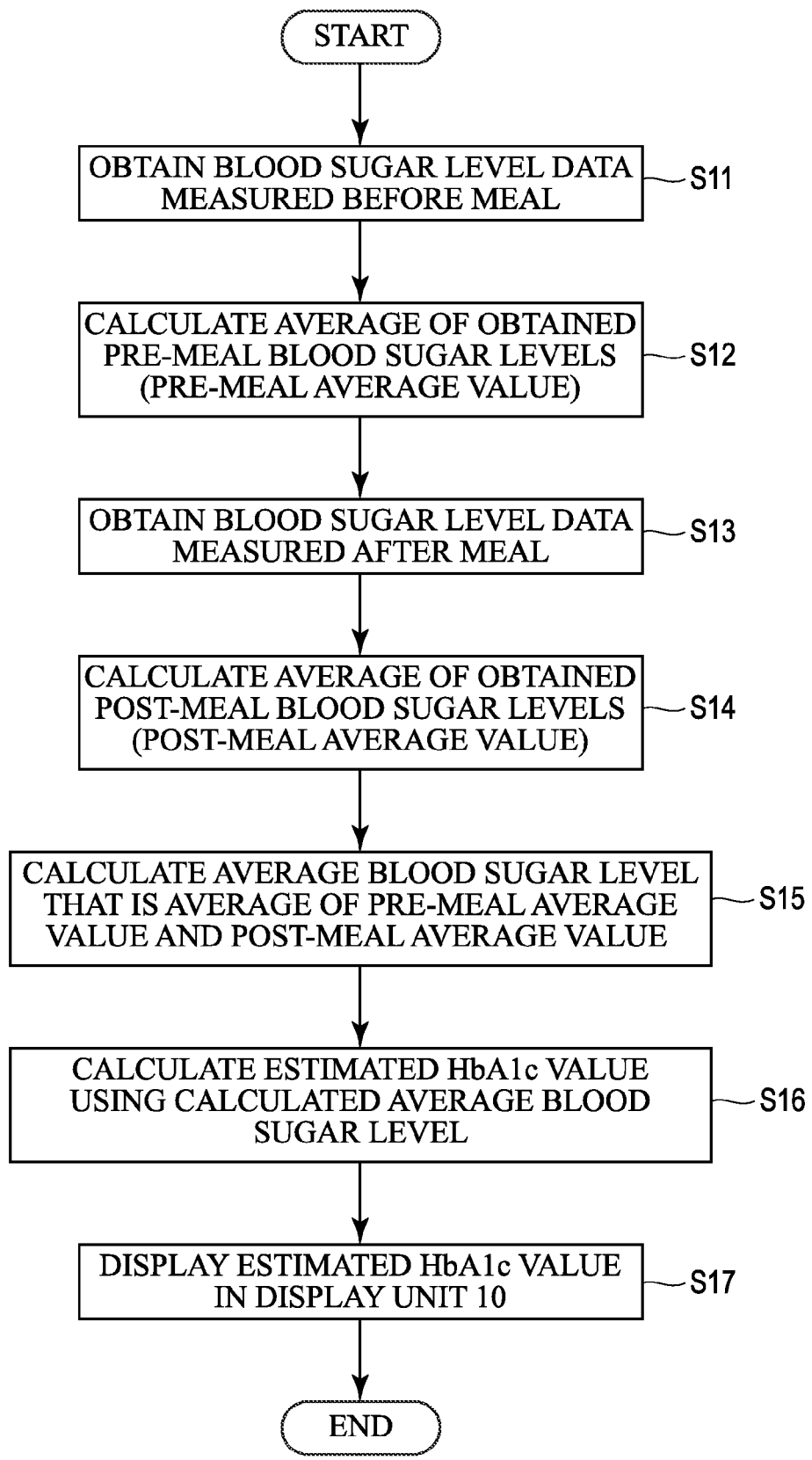
FIG. 4 is a flowchart illustrating operations performed when the blood sugar monitor 1 shown in FIG. 1 is in an HbA1c display mode.

FIG. 4 is a flowchart illustrating operations performed when the blood sugar monitor 1 shown in FIG. 1 is operating in the HbA1c display mode. The steps shown in FIG. 4 are realized by the CPU of the control unit 22 executing a program stored in the ROM.

Note that the flow in FIG. 4 assumes that a plurality of instances of blood sugar level data with which the pre-meal information is associated and a plurality of instances of blood sugar level data with which the post-meal information is associated (one to two months' worth, ideally) are stored in the memory unit 23.

First, the control unit 22 reads out and obtains the blood sugar level data measured before meals (called "pre-meal blood sugar data" hereinafter) from the memory unit 23 (step S11).

Specifically, the control unit 22 obtains the blood sugar level data with which the pre-meal information is associated (pre-meal blood sugar levels) from among the blood sugar level data stored in the memory unit 23.

The pre-meal blood sugar levels are measured when the measurement subject's stomach is empty, and are thus values that are close to the measurement subject's minimum blood sugar level.

Next, the control unit 22 calculates an average of the plurality of pre-meal blood sugar levels obtained in step S11 (called a "pre-meal average value" hereinafter) (step S12).

The pre-meal average value is an average of the blood sugar levels measured when the measurement subject's stomach is empty, and is thus a value close to an average value of the measurement subject's minimum blood sugar level over a predetermined period (one to two months, for example).

Next, the control unit 22 reads out and obtains the blood sugar level data measured after meals from the memory unit 23 (step S13).

Specifically, the control unit 22 obtains the blood sugar level data with which the post-meal information is associated (post-meal blood sugar levels) from among the blood sugar level data stored in the memory unit 23.

Next, the control unit 22 calculates an average of the plurality of post-meal blood sugar levels obtained in step S13 (called a "post-meal average value" hereinafter) (step S14).

The post-meal average value is an average of the blood sugar levels measured after the measurement subject has had a meal, and is thus a value close to an average value of the measurement subject's maximum blood sugar level over a predetermined period (one to two months, for example).

Next, the control unit 22 calculates an average of the pre-meal average value and the post-meal average value (step S15).

For example, assuming the pre-meal average value is represented by be_AV and the post-meal average value is represented by af_AV, the control unit 22 calculates an average all_AV through the following Formula (1), (2), or the like.

$$\text{all\_AV} = \{(\text{be\_AV}) + (\text{Af\_AV})\}/2 \quad (1)$$

$$\text{all\_AV} = \alpha(\text{be\_AV}) + (1-\alpha)(\text{Af\_AV}) \quad (2)$$

Here, $0 < \alpha < 1$.

The average all_AV is an average of the average value of the maximum blood sugar level over the predetermined period and the average value of the minimum blood sugar level over the predetermined period. Accordingly, the average all_AV is a value close to the measurement subject's average blood sugar level during the predetermined period.

The relationship between a measurement subject's average blood sugar level and HbA1c is well-known, as discussed in Patent Literature 1 and 2. Accordingly, the control unit 22 calculates an estimated HbA1c value using the average all_AV calculated in step S15 (step S16).

For example, the control unit 22 calculates the estimated HbA1c value through the following Formula (3). The following Formula (3) uses information disclosed in the document Diabetes Care, Volume 31, Number 8, August 2008.

$$\text{HbA1c estimated value}(\%) = \{(\text{all\_AV}) + 46.7\}/28.7 \quad (3)$$

Finally, the control unit 22 stores the calculated estimated HbA1c value in the memory unit 23 in association with the date/time of the calculation, causes the calculated estimated HbA1c value to be displayed in the display unit 10, and ends the process.

Regarding the format in which the estimated HbA1c value is displayed in the display unit 10, the calculated value may be displayed as-is, or the calculated value may be displayed in a manner that enables comparisons with past calculated values, displayed along with a target HbA1c value set in advance, and so on. The configuration may be such that the measurement subject can input the target HbA1c value using the operating section 11.

Figure 5:
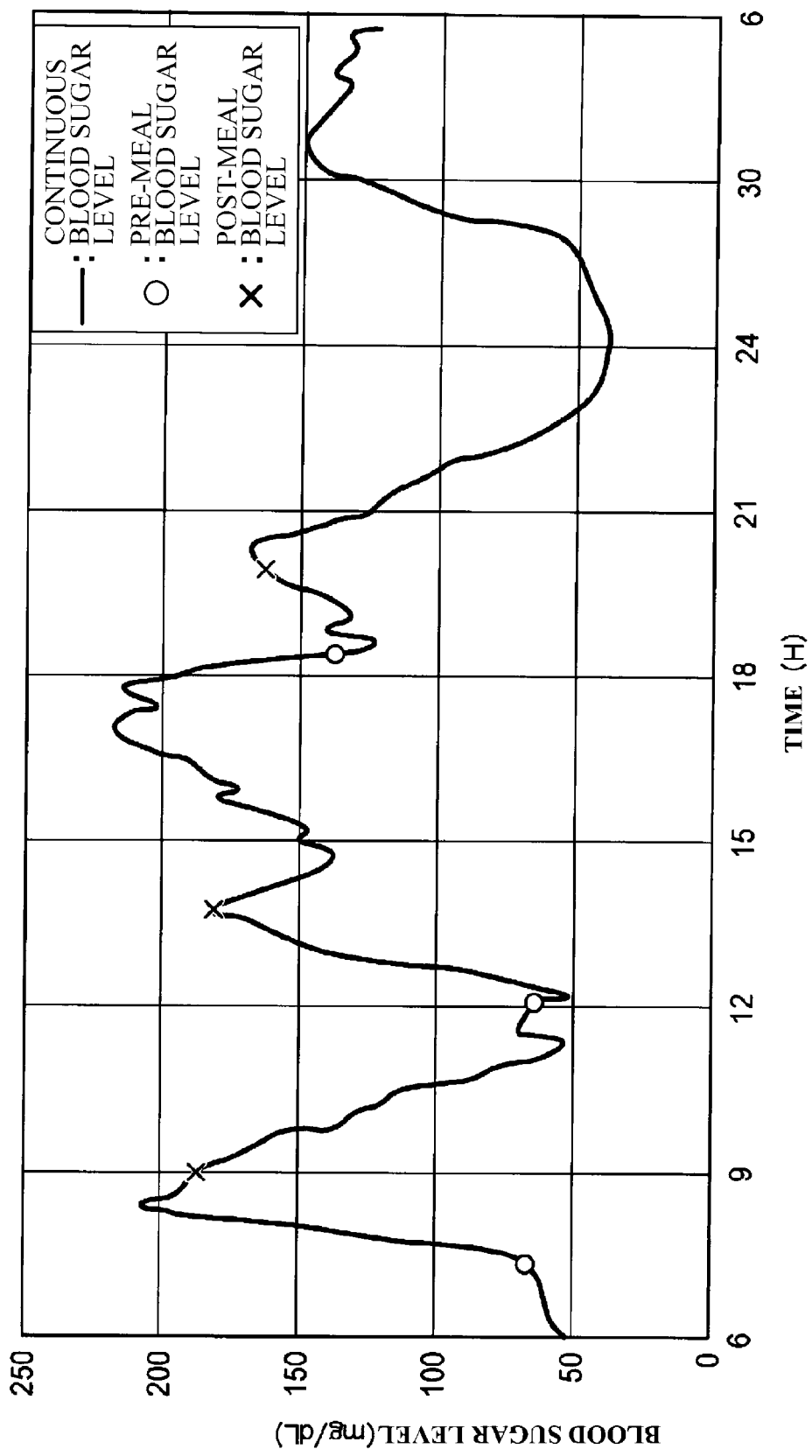
FIG. 5 is a diagram illustrating a measurement subject's continuous blood sugar level measurement data.

FIG. 5 is a diagram illustrating changes in a measurement subject's blood sugar level over the course of a day, as measured by a continuous glucose measurement system (CGMS).

As shown in FIG. 5, the blood sugar level varies greatly even over the course of a single day. An average value (average blood sugar level) of a continuous blood sugar level over the course of a single day, as indicated by the solid line waveform shown in FIG. 5, is 127 mg/dL. If this average value can be measured, the estimated HbA1c value found through the aforementioned Formula (3) can be brought as close to a measured HbA1c value obtained through a blood test as possible.

However, continuous blood sugar level data such as that shown in FIG. 5 is required for an accurate measurement of the measurement subject's average blood sugar level, and such data cannot be obtained from a simple blood sugar monitor or the like.

Accordingly, by finding an average value of the data corresponding to the peaks in the continuous blood sugar level waveform shown in FIG. 5 and an average value of the data corresponding to the valleys in the continuous blood sugar level waveform shown in FIG. 5, and then averaging those average values, the blood sugar monitor 1 according to the present embodiment calculates (estimates) the average blood sugar level with a high level of accuracy.

The data at the areas of the peaks in the continuous blood sugar level waveform shown in FIG. 5 is data near what is known as the "maximum blood sugar level". The blood sugar level often hits the maximum between 60 and 120 minutes (90 minutes, on average) after a meal. Accordingly, recommending that the measurement subject measures the blood sugar level between 60 and 120 minutes following meals makes it possible to bring the aforementioned post-meal blood sugar level closer to the maximum blood sugar level.

Meanwhile, the data at the areas of the valleys in the continuous blood sugar level waveform shown in FIG. 5 is data near what is known as the "minimum blood sugar level". The blood sugar level often hits a minimum when the measurement subject's stomach is empty, and thus the aforementioned pre-meal blood sugar level is data near the minimum blood sugar level.

Note that a method that takes an average of the plurality of pre-meal blood sugar levels and the plurality of post-meal blood sugar levels as the average blood sugar level can also be considered.

However, in the case where the numbers of pre-meal blood sugar levels and post-meal blood sugar levels are different, this method will skew the average blood sugar level toward the data with the higher number. Accordingly, taking an average of the average value of the pre-meal blood sugar levels and the average value of the post-meal blood sugar levels as the average blood sugar level makes it possible to calculate a more accurate average blood sugar level without being concerned with such differences in the numbers of the pre-meal blood sugar levels and the post-meal blood sugar levels.

The blood sugar levels indicated by ○ in FIG. 5 correspond to data measured before meals. The blood sugar levels indicated by x in FIG. 5 correspond to data measured 90 minutes after meals.

The average of the average value of the three blood sugar levels indicated by ○ in FIG. 5 and the average value of the three blood sugar levels indicated by x in FIG. 5 is 133 mg/dL.

Because the average blood sugar level obtained from the data measured by a CGMS is 127 mg/dL as described above, it can be seen that the blood sugar monitor 1 according to the present embodiment is capable of estimating the average blood sugar level at an accuracy within 10% of the actual average blood sugar level.

Meanwhile, because the estimated HbA1c value found using Formula (3) is 6.1% when the average blood sugar level is 133 mg/dL and is 6.3% when the average blood sugar level is 127 mg/dL, the difference therebetween is only 0.2%, which shows that the method according to the present embodiment can estimate HbA1c with a high level of accuracy.

As described thus far, the blood sugar monitor 1 according to the present embodiment calculates, as the average blood sugar level, the average of the average value of the post-meal blood sugar level, which corresponds to the measurement subject's maximum blood sugar level, over the predetermined period, and the average value of the pre-meal blood sugar level, which corresponds to the measurement subject's minimum blood sugar level, over the predetermined period. The estimated HbA1c value is then calculated using the average blood sugar level. Accordingly, an estimated HbA1c value that is close to the actual HbA1c value can be obtained without using a complex system such as a CGMS.

In this manner, changes in HbA1c can be confirmed with ease through the blood sugar monitor 1, which can be easily used at home, which in turn makes it possible to achieve such effects as increasing a patient's motivation with respect to diabetes treatment, helping the patient establish a habit of measuring his/her blood sugar level, and improving the patient's self-management.

Furthermore, according to the blood sugar monitor 1, the blood sugar level with which the pre-meal information is associated is obtained as the pre-meal blood sugar level, the blood sugar level with which the post-meal information is associated is obtained as the post-meal blood sugar level, and these levels are used in the calculations thereafter; accordingly, the data of blood sugar levels measured before meals and the data of blood sugar levels measured after meals can be obtained accurately, making it possible to increase the accuracy with which the estimated HbA1c value is calculated.

Note that as shown in FIG. 5, the blood sugar level varies greatly after meals, and thus the blood sugar level will differ depending on how many minutes after the meal the measurement is taken.

To obtain a more accurate estimated HbA1c value, it is desirable to be able to measure the blood sugar level when the blood sugar level is highest after meals. However, when the blood sugar level is highest differs depending on the actual food eaten, the measurement subject's physical condition, and so on, and it is thus difficult to measure the blood sugar level consistently at that timing.

Accordingly, rather than calculating the average blood sugar level from the averages of the pre-meal average values and the post-meal average values, the control unit 22 of the blood sugar monitor 1 may calculate the average blood sugar level from an average of the pre-meal average value and a maximum value of a plurality of the post-meal blood sugar levels (a post-meal maximum value).

Figure 6:
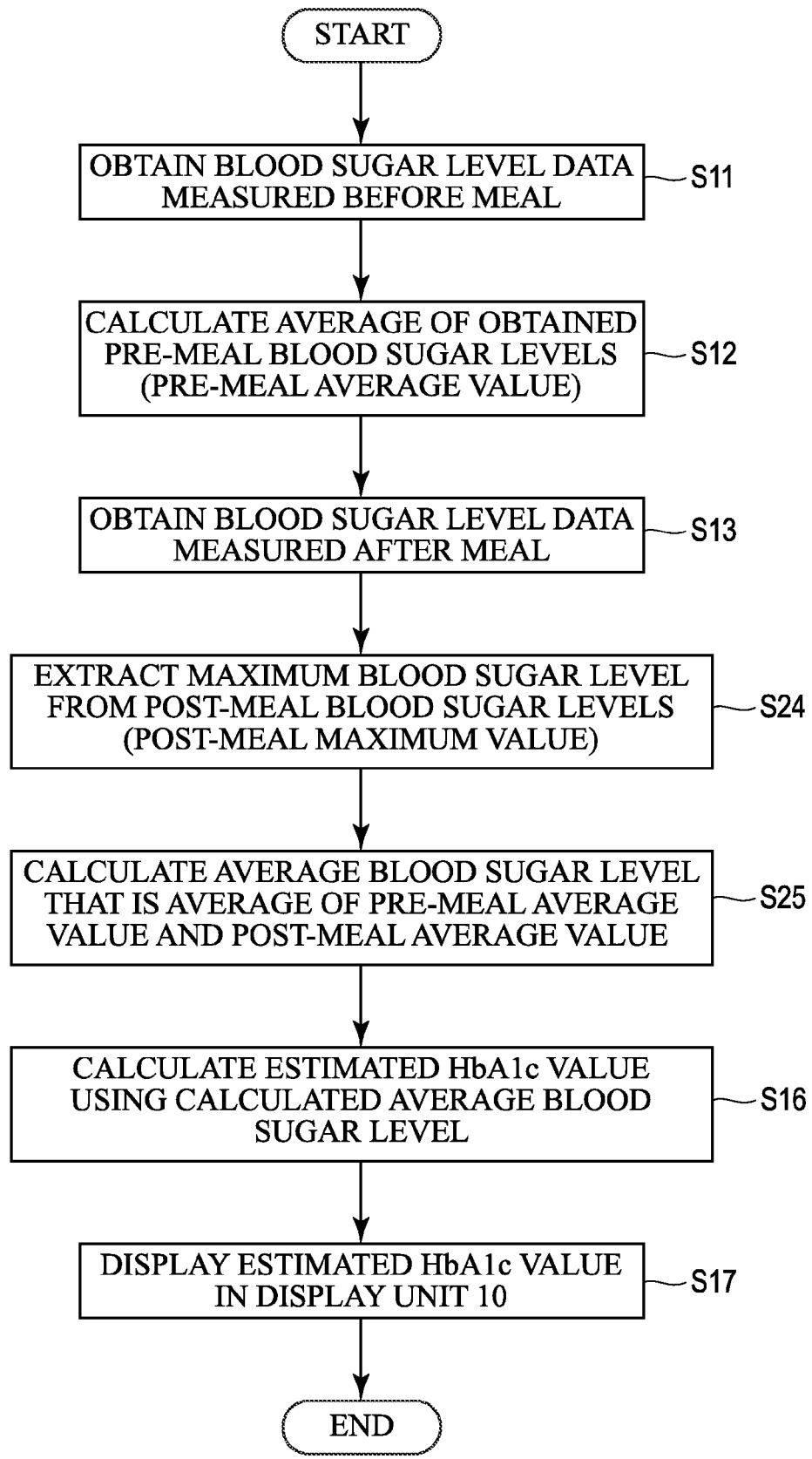
FIG. 6 is a flowchart illustrating a variation on operations performed when the blood sugar monitor 1 shown in FIG. 1 is in an HbA1c display mode.

FIG. 6 is a flowchart illustrating a variation on operations performed when the blood sugar monitor 1 shown in FIG. 1 is operating in the HbA1c display mode. In FIG. 6, step S14 shown in FIG. 4 has been changed to step S24, and step S15 has been changed to step S25.

In step S24, the control unit 22 extracts the post-meal blood sugar level where the blood sugar level is highest (the post-meal maximum value) from the plurality of post-meal blood sugar levels obtained in step S13.

Then, in step S25, the control unit 22 calculates an average of the pre-meal average value and the post-meal maximum value extracted in step S24 as the average blood sugar level.

Then, the control unit 22 calculates the estimated HbA1c value using the average blood sugar level in step S16, causes the estimated HbA1c value to be displayed in the display unit 10, and ends the process.

For example, it is assumed that the data obtained in step S11 is the data indicated by ○ in FIG. 5 and the data obtained in step S13 is the data indicated by x in FIG. 5.

Thus in step S25, the control unit 22 calculates an average of the average value of the three blood sugar levels indicated by ○ in FIG. 5 and the highest of the three blood sugar levels indicated by x in FIG. 5 (138 mg/dL).

Because the average blood sugar level obtained from the data measured by a CGMS is 127 mg/dL as described above, it can be seen that according to the variation illustrated in FIG. 6, the average blood sugar level can be estimated at an accuracy within 10% of the actual average blood sugar level.

Meanwhile, because the HbA1c found using Formula (3) is 6.1% when the average blood sugar level is 127 mg/dL and is 6.4% when the average blood sugar level is 138 mg/dL, the difference therebetween is only 0.3%, which shows that this variation can estimate HbA1c with a high level of accuracy as well.

In this manner, using the highest of the post-meal blood sugar levels instead of the post-meal average value makes it possible to obtain an estimated HbA1c value that is close to the actual HbA1c. In the case where the highest post-meal blood sugar level is used, the average blood sugar level can be found using a numerical value close to the maximum blood sugar level, and thus the accuracy with which the HbA1c is estimated can be improved, as compared to the case where the post-meal average value is used.

Note that according to the variation shown in FIG. 6, it is possible that a post-meal blood sugar level obtained through a measurement taken after the measurement subject has eaten excessively will be extracted as the post-meal maximum value and used in the calculation of the estimated HbA1c value. In such a case, the estimated HbA1c value will not reflect the maximum blood sugar level in the measurement subject's normal daily life.

Accordingly, it is preferable for the control unit 22 to determine the post-meal maximum value having excluded post-meal blood sugar levels that are different from the average value of all post-meal blood sugar levels by greater than or equal to a threshold.

Doing so makes it possible to calculate the estimated HbA1c value without being influenced by spikes in the blood sugar level caused by excessive eating, which in turn makes it possible to improve the reliability of the estimated HbA1c value.

Although the foregoing describes the pre-meal button 11D and the post-meal button 11E as being configured as physical buttons, these buttons may instead by configured as icons displayed in the display unit 10. Note that it is also possible to omit the post-meal button 11E.

As described earlier, the blood sugar level often hits the maximum between 60 and 120 minutes (90 minutes, on average) following a meal. Accordingly, the configuration may be such that an average amount of time required for meals can be set in advance, and blood sugar level data measured within a predetermined amount of time before and after a reference time after {(average amount of time required for meals)+(average amount of time required for blood sugar level to reach a maximum)} has elapsed following the measurement of the pre-meal blood sugar level can be handled as the post-meal blood sugar level.

In other words, in the case where the post-meal button 11E is omitted, in step S13 of FIGS. 4 and 5, the control unit 22 obtains, as the post-meal blood sugar level, a blood sugar level, from the blood sugar levels with which the pre-meal information and the post-meal information are not associated, that was measured at a time after a first amount of time has elapsed after the time at which the pre-meal blood sugar level was measured but before a second time that is longer than the first time has elapsed. Doing so makes it possible to obtain the post-meal blood sugar level even if the post-meal button 11E is not provided.

Furthermore, although the foregoing describes the pre-meal information or the post-meal information as being inputted after the blood sugar level is measured, the configuration may be such that the pre-meal information or the post-meal information can be inputted before the blood sugar level is measured.

The value of a in Formula (2) may be set in accordance with the number of instances of pre-meal blood sugar level data and the number of instances of post-meal blood sugar level data. For example, in the case where the number of instances of pre-meal blood sugar level data is higher than the number of instances of post-meal blood sugar level data, the value of a may be set to be greater than 0.5, whereas in the case where the number of instances of pre-meal blood sugar level data is lower than the number of instances of post-meal blood sugar level data, the value of a may be set to be less than or equal to 0.5, or the like.

The functions realized by the control unit 22 in the present embodiment can also be realized by a generic computer.

For example, the configuration may be such that a unit including the blood sugar level measurement unit 21 shown in FIG. 2 is used as an external unit in a computer that contains the memory unit 23 and to which the display unit 10 and the operating section 11 are connected.

In this configuration, the unit is made controllable from the computer, and the computer stores blood sugar level data sent from the unit in the memory unit 23. The same functions as those of the blood sugar monitor 1 described in the present embodiment can then be realized by the computer executing the processes in the steps shown in FIGS. 4 and 6 using the data stored in the memory unit 23.

The steps shown in FIGS. 4 and 6 and executed by the control unit 22 in the present embodiment can also be provided as a program for execution by a computer. Such a program is then recorded in a non-transitory recording medium from which the computer can read the program.

This computer-readable recording medium includes optical media such as a Compact Disc-ROM (CD-ROM), magnetic recording media such as memory cards, and so on. Further still, the program can be downloaded via a network and provided in such form.

Note that the embodiment disclosed above is to be understood as being in all ways exemplary and in no way limiting. The scope of the present invention is defined not by the aforementioned descriptions but by the scope of the appended claims, and all changes that fall within the same essential spirit as the scope of the claims are intended to be included therein as well.

As described thus far, the following items are disclosed in the present specification.

A diabetes treatment support apparatus disclosed here is a diabetes treatment support apparatus that calculates an estimated HbA1c value using a plurality of instances of blood sugar level data accumulated in a storage unit, and includes: a data obtainment unit that obtains, from the storage unit, data of a plurality of pre-meal blood sugar levels that are blood sugar levels measured before meals and data of a plurality of post-meal blood sugar levels that are blood sugar levels measured after meals; a pre-meal average calculation unit that calculates a pre-meal average value that is an average value of the plurality of pre-meal blood sugar levels obtained by the data obtainment unit; a computation unit that finds a post-meal average value that is an average value of the plurality of post-meal blood sugar levels obtained by the data obtainment unit or finds a maximum post-meal blood sugar level that is a maximum value in the plurality of post-meal blood sugar levels; an average blood sugar level calculation unit that calculates an average blood sugar level using the pre-meal average value and using the post-meal average value or the maximum post-meal blood sugar level; an estimated HbA1c value calculation unit that calculates the estimated HbA1c value using the average blood sugar level; and an output unit that outputs the calculated estimated HbA1c value.

In the diabetes treatment support apparatus disclosed here, the plurality of instances of blood sugar level data accumulated in the storage unit are stored in association with information indicating times at which that data was measured, and the computation unit finds the maximum post-meal blood sugar level from among the post-meal blood sugar levels excluding post-meal blood sugar levels different from an average value of the plurality of post-meal blood sugar levels by greater than or equal to a threshold.

The diabetes treatment support apparatus disclosed here further includes: a blood sugar level measurement unit that measures a blood sugar level of a measurement subject; a first operating unit for inputting pre-meal information indicating a blood sugar level measurement taken before a meal; a second operating unit for inputting post-meal information indicating a blood sugar level measurement taken after a meal; and a storage control unit that stores, in the storage unit, the pre-meal information or the post-meal information inputted before the start of the blood sugar level measurement performed by the blood sugar level measurement unit or after the end of the blood sugar level measurement performed by the blood sugar level measurement unit, in association with blood sugar level data obtained through the measurement, wherein the data obtainment unit obtains the blood sugar level data associated with the pre-meal information as the pre-meal blood sugar level data and obtains the blood sugar level data associated with the post-meal information as the post-meal blood sugar level data.

The diabetes treatment support apparatus disclosed here further includes: a blood sugar level measurement unit that measures a blood sugar level of a measurement subject; a first operating unit for inputting pre-meal information indicating a blood sugar level measurement taken before a meal; and a storage control unit that stores the pre-meal information inputted before the start of the blood sugar level measurement performed by the blood sugar level measurement unit or after the end of the blood sugar level measurement performed by the blood sugar level measurement unit in the storage unit in association with blood sugar level data obtained through the measurement, and stores information indicating a time at which the blood sugar level data measured by the blood sugar level measurement unit was measured in the storage unit, wherein the data obtainment unit obtains the blood sugar level data associated with the pre-meal information as the pre-meal blood sugar level data, and obtains, as the post-meal blood sugar level data, blood sugar level data measured at a time after a first amount of time has elapsed following the time at which the blood sugar level data associated with the pre-meal information was measured but before a second amount of time that is longer than the first amount of time has elapsed.

A diabetes treatment support method disclosed here is a diabetes treatment support method that calculates an estimated HbA1c value using a plurality of instances of blood sugar level data accumulated in a storage unit, the method including: a data obtainment step of obtaining, from the storage unit, data of a plurality of pre-meal blood sugar levels that are blood sugar levels measured before meals and data of a plurality of post-meal blood sugar levels that are blood sugar levels measured after meals; a pre-meal average calculation step of calculating a pre-meal average value that is an average value of the plurality of pre-meal blood sugar levels that have been obtained; a computation step of finding a post-meal average value that is an average value of the plurality of post-meal blood sugar levels that have been obtained or finding a maximum post-meal blood sugar level that is a maximum value in the plurality of post-meal blood sugar levels; an average blood sugar level calculation step of calculating an average blood sugar level using the pre-meal average value and using the post-meal average value or the maximum post-meal blood sugar level; an estimated HbA1c value calculation step of calculating the estimated HbA1c value using the average blood sugar level; and an output step of outputting the calculated estimated HbA1c value.

A diabetes treatment support program disclosed here is a program for causing a computer to execute the steps of the aforementioned diabetes treatment support method.

INDUSTRIAL APPLICABILITY

The present invention can be applied in household blood sugar monitors, for example, and is useful in managing a user's health.

While the present invention has been described in detail with reference to a specific embodiment, it will be clear to one skilled in the art that many variations and modifications can be made without departing from the essential spirit and scope of the present invention. This application claims the benefit of Japanese Patent Application No. 2012-54382, filed Mar. 12, 2012, which is hereby incorporated by reference herein in its entirety.

REFERENCE SIGNS LIST 1 blood sugar monitor
10 display unit 11 operating section
12 electrode insertion section
11D pre-meal button
11E post-meal button
21 blood sugar level measurement unit
22 control unit
23 memory unit

The invention claimed is:

1. A diabetes treatment support apparatus that calculates an estimated HbA1c value using a plurality of instances of blood sugar level data accumulated in a storage unit, the apparatus comprising:
   a data obtainment unit, implemented using a controller, that obtains, from the storage unit, data of a plurality of pre-meal blood sugar levels that are blood sugar levels measured before meals and data of a plurality of post-meal blood sugar levels that are blood sugar levels measured after meals;
   a pre-meal average calculation unit, implemented using the controller, that calculates a pre-meal average value that is an average value of the plurality of pre-meal blood sugar levels obtained by the data obtainment unit;
   a computation unit, implemented using the controller, that finds a maximum post-meal blood sugar level that is a maximum value in the plurality of post-meal blood sugar levels;
   an average blood sugar level calculation unit, implemented using the controller, that calculates an average blood sugar level using the pre-meal average value and using the maximum post-meal blood sugar level;
   an estimated HbA1c value calculation unit, implemented using the controller, that calculates the estimated HbA1c value using the average blood sugar level; and
   an output unit that outputs the calculated estimated HbA1c value.

2. The diabetes treatment support apparatus according to claim 1,
   wherein the plurality of instances of blood sugar level data accumulated in the storage unit are stored in association with information indicating times at which that data was measured; and
   the computation unit, implemented using the controller, finds the maximum post-meal blood sugar level from among the post-meal blood sugar levels excluding post-meal blood sugar levels different from an average value of the plurality of post-meal blood sugar levels by greater than or equal to a threshold.

3. The diabetes treatment support apparatus according to claim 2, further comprising:
   a blood sugar level measurement unit, implemented using an electrode, that measures a blood sugar level of a measurement subject;
   a first operating unit, implemented using the controller, for inputting pre-meal information indicating a blood sugar level measurement taken before a meal;
   a second operating unit, implemented using the controller, for inputting post-meal information indicating a blood sugar level measurement taken after a meal; and
   a storage control unit, implemented using the controller, that stores, in the storage unit, the pre-meal information or the post-meal information inputted before the start of the blood sugar level measurement performed by the blood sugar level measurement unit or after the end of the blood sugar level measurement performed by the blood sugar level measurement unit, in association with blood sugar level data obtained through the measurement,
   wherein the data obtainment unit, implemented using the controller, obtains the blood sugar level data associated with the pre-meal information as the pre-meal blood sugar level data and obtains the blood sugar level data associated with the post-meal information as the post-meal blood sugar level data.

4. The diabetes treatment support apparatus according to claim 2, further comprising:
   a blood sugar level measurement unit, implemented using an electrode, that measures a blood sugar level of a measurement subject;
   a first operating unit, implemented using the controller, for inputting pre-meal information indicating a blood sugar level measurement taken before a meal; and
   a storage control unit, implemented using the controller, that stores the pre-meal information inputted before the start of the blood sugar level measurement performed by the blood sugar level measurement unit or after the end of the blood sugar level measurement performed by the blood sugar level measurement unit in the storage unit in association with blood sugar level data obtained through the measurement, and stores information indicating a time at which the blood sugar level data measured by the blood sugar level measurement unit was measured in the storage unit,
   wherein the data obtainment unit, implemented using the controller, obtains the blood sugar level data associated with the pre-meal information as the pre-meal blood sugar level data, and obtains, as the post-meal blood sugar level data, blood sugar level data measured at a time after a first amount of time has elapsed following the time at which the blood sugar level data associated with the pre-meal information was measured but before a second amount of time that is longer than the first amount of time has elapsed.

5. The diabetes treatment support apparatus according to claim 1, further comprising:
   a blood sugar level measurement unit that measures, implemented using an electrode, a blood sugar level of a measurement subject;
   a first operating unit, implemented using the controller, for inputting pre-meal information indicating a blood sugar level measurement taken before a meal;
   a second operating unit, implemented using the controller, for inputting post-meal information indicating a blood sugar level measurement taken after a meal; and
   a storage control unit, implemented using the controller, that stores, in the storage unit, the pre-meal information or the post-meal information inputted before the start of the blood sugar level measurement performed by the blood sugar level measurement unit or after the end of the blood sugar level measurement performed by the blood sugar level measurement unit, in association with blood sugar level data obtained through the measurement,
   wherein the data obtainment unit, implemented using the controller, obtains the blood sugar level data associated with the pre-meal information as the pre-meal blood sugar level data and obtains the blood sugar level data associated with the post-meal information as the post-meal blood sugar level data.

6. The diabetes treatment support apparatus according to claim 1, further comprising:
   a blood sugar level measurement unit, implemented using an electrode, that measures a blood sugar level of a measurement subject;

a first operating unit, implemented using the controller, for inputting pre-meal information indicating a blood sugar level measurement taken before a meal; and a storage control unit, implemented using the controller, that stores the pre-meal information inputted before the start of the blood sugar level measurement performed by the blood sugar level measurement unit or after the end of the blood sugar level measurement performed by the blood sugar level measurement unit in the storage unit in association with blood sugar level data obtained through the measurement, and stores information indicating a time at which the blood sugar level data measured by the blood sugar level measurement unit was measured in the storage unit, wherein the data obtainment unit, implemented using the controller, obtains the blood sugar level data associated with the pre-meal information as the pre-meal blood sugar level data, and obtains, as the post-meal blood sugar level data, blood sugar level data measured at a time after a first amount of time has elapsed following the time at which the blood sugar level data associated with the pre-meal information was measured but before a second amount of time that is longer than the first amount of time has elapsed.

7. A diabetes treatment support method that calculates an estimated HbA1c value using a plurality of instances of blood sugar level data accumulated in a storage unit, the method comprising:

a data obtainment step of obtaining, from the storage unit, data of a plurality of pre-meal blood sugar levels that are blood sugar levels measured before meals and data of a plurality of post-meal blood sugar levels that are blood sugar levels measured after meals;

a pre-meal average calculation step of calculating a pre-meal average value that is an average value of the plurality of pre-meal blood sugar levels that have been obtained;

a computation step of finding a maximum post-meal blood sugar level that is a maximum value in the plurality of post-meal blood sugar levels;

an average blood sugar level calculation step of calculating an average blood sugar level using the pre-meal average value and using the maximum post-meal blood sugar level;

an estimated HbA1c value calculation step of calculating the estimated HbA1c value using the average blood sugar level; and an output step of outputting the calculated estimated HbA1c value.

8. A diabetes treatment support program for causing a computer to execute the steps of the diabetes treatment support method according to claim 7.

* * * * *